United States Patent [19]

Rha et al.

[11] Patent Number: 5,354,424
[45] Date of Patent: Oct. 11, 1994

[54] PAPER COMPOSITION AND METHODS THEREFOR

[76] Inventors: Chokyun Rha, 285 Commonwealth Ave., Boston, Mass. 02114; Maritta Timonen, Kantelettarentie 8E 57, Helsinki, Finland

[21] Appl. No.: 825,037

[22] Filed: Jan. 24, 1992

Related U.S. Application Data

[63] Continuation-in-part of Ser. No. 743,152, Aug. 9, 1991, and a continuation-in-part of Ser. No. 566,013, Aug. 10, 1990, abandoned, and a continuation-in-part of Ser. No. 565,346, Aug. 10, 1990, abandoned, and a continuation-in-part of Ser. No. 730,029, Jul. 12, 1991, abandoned, and a continuation-in-part of Ser. No. 464,291, Jan. 12, 1990, abandoned, and a continuation-in-part of Ser. No. 370,629, Jun. 23, 1989, abandoned, and a continuation-in-part of Ser. No. 309,387, Feb. 10, 1989, abandoned.

[51] Int. Cl.$^5$ .......................................... D21H 17/25
[52] U.S. Cl. ................................ 162/135; 162/177; 106/169; 427/395
[58] Field of Search .............. 162/175, 176, 177, 178, 162/135; 427/394, 395; 106/169

[56] References Cited

U.S. PATENT DOCUMENTS

| 3,598,622 | 8/1971 | Maher et al. | 106/210 |
| 4,310,360 | 1/1982 | Kvant | 162/177 |
| 5,061,346 | 10/1991 | Taggart et al. | 162/175 |

FOREIGN PATENT DOCUMENTS

| 0147380A3 | 12/1984 | European Pat. Off. . | |
| 0301372A1 | 7/1988 | European Pat. Off. . | |
| 0382576A1 | 2/1990 | European Pat. Off. . | |
| 2636951A1 | 8/1976 | Fed. Rep. of Germany . | |
| 45-13162 | 5/1970 | Japan | 162/177 |
| 53-94610 | 8/1978 | Japan | 162/175 |
| 1035113 | 8/1983 | U.S.S.R. | 162/177 |

*Primary Examiner*—Peter Chin

[57] ABSTRACT

A paper product treated with a degradation product of a polysaccharide derivative comprising a mixture of oligomers of the polysaccharide derivative, a majority of said oligomers having a degree of polymerization such that the oligomer conforms to a rod-like configuration.

67 Claims, 5 Drawing Sheets

PAPER COMPOSITION AND METHODS THEREFOR

This is a continuation-in-part of all of the following co-pending applications: U.S. patent application Ser. No. 07/743,152, filed Aug. 9, 1991, U.S. patent application Ser. No. 07/566,013 filed Aug. 10, 1990, now abandoned, U.S. patent application Ser. No. 07/565,346 filed Aug. 10, 1990, now abandoned, U.S. patent application Ser. No. 07/730,029 filed Jul. 12, 1991, now abandoned, U.S. patent application Ser. No. 07/464 291 filed Jan. 12, 1990, now abandoned, U.S. patent application Ser. No. 07/370,629 filed Jun. 23, 1989, now abandoned, U.S. patent application Ser. No. 07/309,387 filed Feb. 10, 1989, now abandoned. The contents of each of the above-identified applications are hereby expressly incorporated by reference.

The contents of Applicants' co-pending related applications entitled "Polysaccharide Article and Uses Therefor" filed concurrently herewith, and U.S. patent application Ser. No. 07/567,045 filed Aug. 10, 1990 are also expressly incorporated by reference.

FIELD OF THE INVENTION

The present invention relates to the field of paper, pulp and textile making. More particularly, the invention relates to the combination of oligomeric mixtures derived from the degradation of polysaccharide derivatives with cellulose based materials.

BACKGROUND OF THE INVENTION

Of the many raw materials used by the paper and textile industries, cellulose fibers have occupied the dominant position for many years. The techniques of paper making are known worldwide and the basic principles have not changed. Despite great improvements in papermaking, however, procedures for strengthening cellulose fibers in the papermaking process are often expensive, time consuming, and environmentally questionable.

The kraft or sulfate process is probably the most extensively employed method to produce strong cellulose fibers. The active ingredients in pulping wood to its fibrous state are sodium hydroxide and sodium sulfide, in a strong alkaline solution. The process generates objectionable smells from the sodium sulfide produced during the process. Kraft pulps are dark in color, difficult to bleach and very strong.

Nevertheless, cellulose fibers obtained from the pulping process are generally unsuited for paper making and must first be refined. With given pulps, final paper properties are largely controlled by the type and extent of refining action employed. A variety of additive materials can be introduced to the paper-making pulps, commonly called "furnish", during stock preparation. Fillers such as clays, or calcium carbonate are used for the control of sheet opacity and for other reasons. Dyes are used extensively for color control and other additives such as wet-strength agents, and defoamers are used as needed.

For the most part, however, operations designed to increase the strength and/or other physical properties of paper take place subsequent to the paper making operation and are called "off-machine converting." These converting operations are highly complex and include embossing, coating, waxing, laminating, impregnating, saturating, currogating, and printing. For example, food packaging has led to extensive paper utilization with the paper often being coated, waxed, resin-impregnated, or combined with other foils and films. A relatively simple and inexpensive method of improving the paper making process and increasing the stiffness and ultimate strength of paper is needed.

In textile making processes, cotton fibers which are essentially pure cellulose are typically formed first into yarns or threads which are in turn used in waving or non-woven processes to form fabrics or other textile materials. Prior to and during its formation into yarns, threads or otherwise, raw cotton materials are subjected to various processes such as washing, opening, carding, drawing, combing, spinning and other processes well known in the textile making industry. Similar to The paper industry, processes designed to treat raw cotton fibers or articles such as fabric sheets made therefrom are typically complex, expensive and environmentally questionable.

SUMMARY OF THE INVENTION

It is an object of the invention to provide materials that improve the properties of paper, pulp and textile products.

It is a further object of the invention to provide a simplified paper-making process by improving the dewatering and draining properties of paper.

It is yet another object of the present invention to provide degradation products of polysaccharide derivatives which are useful as strengthening and dewatering agents for treating paper products or materials.

The invention discloses the manufacture of novel paper materials comprising treating paper with water soluble or water suspendable mixtures of relatively low molecular weight oligomers. The oligomers are obtained by degrading polysaccharide derivatives, most preferably starch derivatives and cellulose derivatives. Oligomers are relatively short chain polymers derived from degradation of long chain starting material polysaccharide derivatives.

Figure 6:
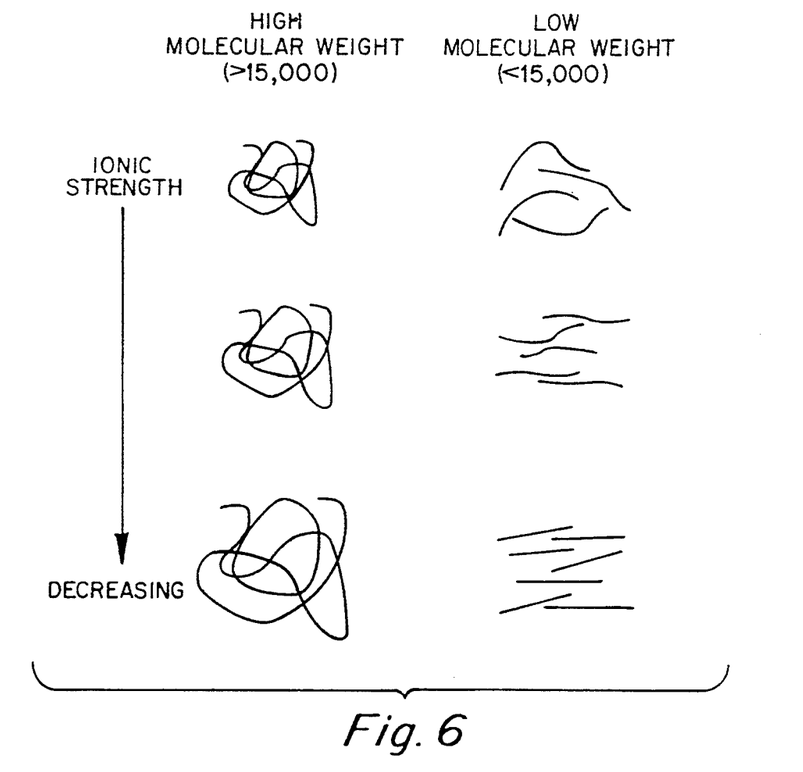
FIG. 6 shows the molecular weight dependent conformation transition in CMC (for both CMC raw materials, $M_w > 15,000$, which are used as starting materials to obtain certain hydrolysates described and CMC hydrolysates, $M_w < 15,000$)

As described in detail below, most preferably the polysaccharide derivative oligomeric mixtures are comprised of a majority of oligomers having a rod-like configuration as opposed to a random-coil configuration, See. FIG. 6. Furthermore most preferably, the oligomeric mixtures are relatively monodisperse, have a polydisperity index of less than about 2.0 and contain less than about 25% by weight, most preferably less than about 10% by weight, of monosaccharides, disaccharides and mixtures thereof.

The invention further pertains to paper products coated or impregnated with water soluble or water dispersable mixtures of relatively low molecular weight oligomers obtained by degrading polysaccharide derivatives. Most preferably these mixtures are obtained by degrading starch or cellulose derivatives.

In accordance with the invention, there is provided a water soluble or water dispersable mixture of polymers derived from a degraded polysaccharide derivative, the mixture of polymers having an average degree of polymerization in the range of about 3 to about 500, preferably 3-300, more preferably 3-100 and most preferably 5-50. The most preferred polysaccharide derivative comprises starch or cellulose. The polysaccharide derivative may be degraded by enzymatic, chemical, physical, or mechanical agents/mechanisms. In embodiments where an enzyme preparation is utilized to perform the degradation, the enzyme preparation is typically selected from the group of polysaccharide degrading enzymes. In the case of starch derivatives, enzymes such as amylases or pullulanases and mixtures thereof are suitable.

In embodiments where degradation of a polysaccharide derivative is to be effected by chemical or physical means, chemical hydrolysis, chemical oxidation and heat treatment are preferred mechanisms for achieving the desired oligomeric mixtures according to the invention.

By conventional means, an initially degraded polysaccharide derivative mixture may be further separated into fractions of oligomers of differing average chain lengths, e.g. using chromatographic techniques. The viscosity of the various fractions will vary with the degree of average chain length of the polymers contained within in a fraction. Depending on the particular paper product application, one or more fractions are selected from an initial oligomeric mixture having a viscosity (average chain length) which is most appropriate for the particular application.

The method of strengthening paper or textile comprises treating the paper or textile with a water soluble or water dispersable mixture of relatively low molecular weight polymers, which polymers are obtained by degrading polysaccharide derivatives, most preferably starch and cellulose.

The method of enhancing the dewatering properties of paper pulp comprises treating the pulp with a water soluble or water dispersable mixture of relatively low molecular weight oligomers, which are obtained by degrading polysaccharide derivatives, most preferably starch derivatives and cellulose derivatives.

DETAILED DESCRIPTION OF THE INVENTION

This invention describes paper materials treated with the degradation product of a polysaccharide derivative and methods therefor.

The C—O—C linkage formed between two joined simple sugar units in a polysaccharide chain is called a glycosidic linkage, and continued condensation of monosaccharide units will result in polysaccharides. The most common polysaccharides are amylose and cellulose, both made up of glucose monomers. Amylose is a major constituent of starch and glycogen. Cellulose is the major structural component of plants. Other polysaccharides useful in this invention have a straight chain or branched polymer backbone including one or more sugar monomers. These polysaccharides include those having sugar monomers such as glucose, galactose, arabinose, mannose, fructose, rahmnose, and xylose.

Preferred polysaccharide derivatives useful in the article and methods of this invention are cellulose derivatives and starch derivatives. Examples of other such polysaccharide derivatives with branched or straight backbones are cartagenan, pullulan, pustulan, laminarin, scleroglucan, alginate, guar gum, gum arabic, inulin, pectin, whelan, rhamsan, gellan, xanthan, zooglan, methylan, chitin, cyclodextrin, chitosan, hemicellulose and beta-glucan.

Preferably, a polysaccharide derivative which has substituents has a degree of derivatization of between about 0.1 and about 3.0. "Degree of substitution" refers to the number of derivative groups (e.g. carboxymethyl, hydroxypropyl) per monomer unit in the polysaccharide backbone (branch or straight chain backbone). A degree of substitution of 0.2 means, for example that there is about one derivative substituent for every five monomer units in the polysaccharide backbone. A degree of substitution of three would mean there are three derivative substituents per every monomer unit in a polysaccharide chain. Typical substituents comprise one or more of sulfate, carboxylic acid (as found, for example, in cartagenan, alginate, pectin), carboxylic ester, pyruvic acid (as found, for example, in pectin, xanthan gum, zooglan, and methylan), carboxymethyl, hydroxypropyl, methyl, methylethyl, hydroxyethyl, hydroxyethylmethyl, hydroxypropylmethyl, hydroxypropylethyl and the like.

Carboxymethyl starch can be degraded enzymatically to produce corresponding carboxymethyl starch hydrolyzates. Other typical suitable starch derivatives include hydroxypropyl, methylethyl and hydroxyethyl starches. The substituents are typically bonded to a starch glucose monomer unit at the 2, 3 and 6 positions. Most typically a starch starting material comprises between about 1% to 85% amylose and about 15% to 99% amylopectin.

Cellulose derivatives are commercially available. Such exemplary products as methylcellulose (MC, Methocel MC, 64630, Fluka Chemie AG, CH-9470 Buchs, Switzerland), hydroxypropylmethylcellulose (HPMC, H-9262, Sigma Chem. Co., St. Louis, Mo.) and carboxymethyl cellulose (CMC 7MFD, Blanose, Hercules Chem. Co., 92507 Rueil-Malmaison Ceder, France) all have a degree of substitution between 0.1 and 3. Hydroxypropyl celluloses are also commercially available and suitable for use.

As described more fully herein, such polysaccharide derivatives may be degraded to polymeric mixtures of average degree of polymerization (DP) between about 3 and about 500 by enzymatic, chemical, physical or mechanical agents/means. The enzymatically derived oligomeric mixtures are generally referred to as a "hydrolyzate." The term "degraded" refers to the more generic procedure whereby polysaccharide derivatives are broken down into smaller polymeric units.

Exemplary enzymes for use in degrading certain of the above described polysaccharide derivatives are pectinases, lyases, lysozymes, xanthanases, chitinases and laminarases. Exemplary enzymes which are suitable for degrading cellulose derivatives are various cellulases. They can be produced from a multitude of different microorganisms such as strains of Trichoderma, Aspergillus, Penicillium, etc. A selected microorganism strain is grown by conventional means in a suitable medium such that the cellulases are produced, the microorganism is separated from the medium, the medium is collected and typically concentrated and dried. Cellulase preparations suitable for use herein are, e.g. the commercially available cellulase preparations designated as the Econase series as produced by Alko Ltd., Helsinki, Finland.

A polysaccharide derivative may also be hydrolyzed by treating a polysaccharide derivative with a solution of acid. Typical acid treatment solutions might typically contain acids such as sulphuric acid, hydrochloric acid, phosphoric acid, or mixtures of the foregoing. The concentration of the acid in the treatment solution and the treatment time and temperature may vary depending on the degree of degradation of the polysaccharide derivative which is desired.

A selected polysaccharide derivative derivative may be degraded by oxidation with such agents as chlorine, oxygen or hydrogen peroxide. Such oxidative treatments and reaction conditions are well known in the art. It may also be possible to use physical methods like heat or mechanical shear treatment or sonication when cleaving the chain backbone of polysaccharide derivatives.

Whatever conventional chemical (hydrolyric, oxidative or otherwise) or physical treatments are employed, the conditions and the degree of treatment are selected such that the polymeric mixture resulting from the initial treatment has an average DP of between about 3 and about 500, preferably 3-300, more preferably 3-100 and most preferably 5-50 at least in the case of CMC.

Enzymes which may be used with respect to paper or textile products prepared or coated with degraded starch derivatives, are various amylolytic enzyme preparations. They can be produced from a multitude of different microorganisms such as strains of Bacillus, Klebsiella, Clostridium, Aspergillus, Rhizopus. Typical commercially available enzyme preparations suitable for use herein are amylolytic preparations (such as alpha and beta amylases), pullulanases, and cyclodextrin glycosyltransferases (CGTase).

The oligomeric mixtures described above are used in the method of the invention to improve the properties of paper and textile products and to strengthen paper and textile products. In its broadest embodiment, the method comprises preparing mixture of substituted polysaccharide derivative oligomers having an average degree of polymerization (DP) in the range of 3-500. Next, the mixture is then contacted with a cellulose based material such as paper for a period of time sufficient To treat the cellulose based material with the polymer mixture.

The terms "paper" and "pulp products" are intended to include a variety of products made primarily from cellulose, synthetic or other fibers, such products being recognized by those skilled in the art as paper, boards, construction paper, and structural matierals made from wood. In addition, these terms refer to articles prepared from cellulose, synthetic, or other fibers or filamentous materials such as those used in the textile industry. Specific examples include felted or matted sheets of cellulose fibers, formed on a fine wire screen from a dilute water suspension, and bonded together as the water is removed and the sheet is dried or woven or non-woven sheets of textile fabric. These terms may also include sheet materials produced from other types of fibers, particularly mineral or synthetic fibers, formed and bonded by other means. These terms also include liquified or semi-solid mixtures of pulped fibers, commonly called "furnish", to which is added various materials such as fillers (clays, calcium carbonate), dyes, wet-strength agents and the like during the typical paper-making process and raw fibrous materials such as cotton which is ultimately formed into a yarn, thread or fabric.

Methods of paper manufacture include the basic steps of pulping fibers, refining the pulp by addition of various materials, as described below, forming the paper on mesh screens, and drying the matted fibers.

The oligomeric mixtures can be applied after the paper is made, in the so-called "off-machine converting" procedures. The mixtures can be applied using methods well known in the art such as dipping, spraying, and rolling.

Not wishing to be bound by any theory, it is believed that an oligomeric polysaccharide derivative mixture thus prepared coats the surface of the paper or textile and becomes fixed thereon by attraction between the oligomeric mixture and the cellulose based components of the paper or textile including by physical forces such as hydrogen bonding, Van der Waals forces and the like. The low molecular weight oligomers of the invention are aligned along the cellulose, or other fibers. As a result, the intermolecular attraction per unit length increases, facilitating the quality of the final product and improving the processability of the paper, textile or pulp product.

The oligomeric mixtures can also be incorporated into paper furnish during pulp refining procedures. In this embodiment, the mixture of degraded polysaccharide derivatives can be incorporated into the pulp furnish along with other dyes, colorants, wet-strength agents (agents capable of increasing the strength of wet or suspended materials), defoamers, and the like. In this procedure, the oligomers will become impregnated into the matrix of the paper fibers.

The term "treated" or "treatment" are intended to include means or methods for contacting paper or textile products with the oligomeric mixtures so that at least one effect of such contact is to strengthen the paper or textile, coat or impregnate the paper or textile, improve the paper, textile or pulp handling properties during manufacturing, and/or increase the dewatering capacity of the paper or textile product.

Paper or textile produced according to the method of this invention may be stronger than non-treated paper or textile. Moreover, treated paper may have less water spreading than untreated paper. Furnish treated with the polymers of the invention show an increased rate of dewatering in the paper during the early stages of draining.

This invention will now be more particularly described using the following examples.

Example 1: General Preparation of a Cellulose Precursor Hydrolyzate

Cellulose derivative hydrolyzates may be prepared from soluble cellulose derivatives as discussed above by an enzymatic hydrolysis utilizing a cellulase preparation having endo- 1, 4- beta-glucanase as the sole active hydrolyric agent. The average degree of polymerization (DP) of the polymers formed by such a hydrolysis is less than about 500, and thus the viscosity of solutions of the hydrolyzate is reduced significantly compared to the viscosity of solutions of the unhydrolysed cellulose derivatives. The specific conditions suitable for and the specific time sufficient to secure the desired hydrolysis may be readily determined for each selected cellulose derivative and each selected enzyme preparation.

Similarly in other embodiments of the invention where degradation is carried out using chemical or physical means, the average DP of the polymers is less than 500 and the viscosity of the resulting mixture is significantly reduced.

Example 2: Preparation of Typical Cellulose Derivative Enzyme Hydrolyzates Containing Small Amounts of Mono- and Disaccharides Having Low Viscosity a. Methylcellulose hydrolyzate 30 g of methylcellulose (MC, Methocel MC, 64630, Fluka Chemie AG, CH-9470 Buchs, Switzerland) was mixed in 3 l of water and the pH of the solution was adjusted to 5.5 with 15% phosphoric acid and the temperature was raised to 40° C. 0.3 ml of an enzyme preparation from Trichoderma reesei, Econase CE (as so designated by Alko Ltd., Helsinki, Finland) having a total endo-1, 4 beta-glucanase activity of 1680 nkat from which the beta-glucosidase activity was removed chromatographically was added to the solution. After hydrolysis for 24 hours the enzyme was inactivated by heating (90° C., 15 min.). The hydrolyzate solution was subsequently cooled and freeze-dried.

The hydrolyzate product contained less than 0.5% by weight of glucose and cellobiose.

b. Hydroxypropylmethylcellulose hydrolyzate 20 g of hydroxypropylmethylcellulose (HPMC, H-9262, Sigma Chemical Company, St. Louis, Mo., U.S.A.) was mixed in 1 l of water and the pH of the solution was adjusted to 5.5 with 15% phosphoric acid and the temperature was raised to 40° C. 0.24 ml of the enzyme preparation described above having a total endo-1, 4 beta-glucanase activity of 1340 nkat from which the beta-glucosidase activity was removed chromatographically (as described above) was added to the solution. After two hours another 20 g of hydroxypropylmethylcellulose was added to the solution. After the hydrolysis of 22 hours the enzyme was inactivated by heating (90° C., 15 min.). Finally the hydrolyzate solution was cooled and freeze-dried.

The product contained less than 0.05% by weight of glucose and cellobiose.

c. Carboxymethylcellulose hydrolyzate (i) Hydrolysis with Trichoderma reesei derived enzyme preparation 20 kg of carboxymethylcellulose (CMC 7MFD-type, a cellulose gum, also designated by the tradename Blanose and available from Hercules Chemical Company, 92507, Rueil-Malmaison Ceder, France; 7MFD designates a medium viscosity, food grade carboxymethylcellulose having 7 out of 10 glucose units substituted with carboxymethyl) was mixed in 320 l of water and the pH of the solution was adjusted to 5.5 with 15% phosphoric acid and the temperature was raised to 40° C. About 0.27 l of the enzyme preparation described above having a total endo-1, 4 beta-glucanase activity of 1,780,000 nkat from which the beta-glucosidase activity was removed chromatographically (as described above) was added to the CMC solution. After one hour another 23 kg of CMC was added to the solution. After hydrolysis of 23 hours the enzyme was inactivated by heating (90° C., 15 min.). Finally, the hydrolysis solution was concentrated by conventional evaporating and spray-drying.

The product contained less than 2% by weight of glucose and cellobiose. When the same hydrolysis was carried out with the original cellulase enzyme preparation of Trichoderma reesei-fungus, the amount of produced glucose and cellobiose was above 5% by weight.

(ii) Hydrolysis with Aspergillus and Penicillium derived enzyme preparations

The enzyme preparations selected were commercially available Cellulase AP 3 (Amano Pharmaceutical Co., Ltd., Nagoya, Japan) produced using an Aspergillus strain and Cellulase CP (Sturge Enzymes, North Yorkshire, England) produced using a Penicillium strain. Carboxymethylcellulose hydrolyzates were prepared as described in Example c(i), except that 30 g of CMC-7MFD was used in 1 l of water, and the amounts of enzymes added were 0.028 g of Cellulase AP 3 (having a total endo-1, 4 beta-glucanase activity of 1350 nkat) and 0.048 g of Cellulase CP (having a total endo-1, 4 beta-glucanase activity of 1350 nkat). The viscosities and molecular weight distributions of the hydrolyzates produced by either cellulase were similar to the hydrolyzate produced with enzymes derived from Trichoderma reesei.

The viscosities of the various cellulose derivatives and their hydrolyzates as described above were measured using a Haake-Rotovisco viscometer with sensor systems NV (Karlsruhe, Federal Republic of Germany) (Table 1). The viscosities were measured in water solutions at 25° C. Table 1 sets forth the concentrations (by weight) of a variety of solutions all having the same viscosity.

TABLE 1

Concentrations of cellulose derivatives and their respective hydrolyzates in solution all having a viscosity of 20 mPa·s (milli-Pascals-second) at 25° C.

| Cellulose Derivative | Concentration (by weight) |
|---|---|
| Methylcellulose | 2% |
| Methylcellulose hydrolyzate | 5% |
| Hydroxypropylmethylcellulose | 3% |

TABLE 1-continued

Concentrations of cellulose derivatives and their respective hydrolyzates in solution all having a viscosity of 20 mPa·s (milli-Pascals-second) at 25° C.

| Cellulose Derivative | Concentration (by weight) |
|---|---|
| Hydroxypropylmethylcellulose hydrolyzate | 10% |
| Carboxymethylcellulose | 2% |
| Carboxymethylcellulose hydrolyzate | 20% |

As the data in Table 1 indicate, the hydrolyzate of a cellulose derivative has a substantially lower viscosity than an equal amount by weight in aqueous solution of the cellulose derivative itself. As described below, in most preferred embodiments, oligomeric mixtures have a viscosity low enough such that the oligomers have a rod-like configuration.

Example 3: Carboxymethylcellulose Chemical Hydrolysis 2 gms of carboxymethylcellulose (Blanose Cellulose Gum 7 LFD, Hercules Chemical Co., 92507, Rueil-Malmaison Cedar, France) was hydrolyzed for about one hour in 100 ml of 1M sulphuric acid solution at about 100° C. After hydrolysis the solution was cooled to about room temperature, neutralized to about pH 6 with 25 ml of 25% (w/w) of NaOH solution and freeze-dried. This hydrolysis treatment produced a mixture of polymers containing less than about 4% by weight of saccharides (cellobiose and glucose). The viscosity (and average DP) of this hydrolyzate is similar to the viscosities (and average DP) of the hydrolyzates produced by the enzymatic treatments described above utilizing enzymes derived from *Trichoderma reesei*.

Rod-Like Configuration of Preferred Oligomers

Chain conformation of oligomers can be evaluated from the molecular weight (or DP) dependency of intrinsic viscosity of a solution of oligomers using the Mark-Houwink equation:

$$[\mu] = KM^a$$

where $[\mu]$ is the intrinsic viscosity, M is the molecular weight, and K and a are constants. The constant a of this equation provides an indication of the chain conformation of a polymer or oligomer. The DP of an oligomer or average DP of a mixture of oligomers is simply calculated from the molecular weight of the oligomer(s) divided by the molecular weight of a monomer unit of the oligomer (about 220 for CMC).

Initially, approximate viscosity average molecular weights ($M_v$) and average DPs of a series of typical CMC oligomeric mixtures designated EP 1511, 1512, 151/49, 151/51, 151/52 were first calculated from the Mark-Houwink equation based on previously reported literature values (*Brown and Henley*, 1964) for the K and a components of the equation. Such calculated molecular weights and average DPs are reported in Table 2.

Subsequently the weight average molecular weights ($M_w$) of a variety of typical oligomeric mixtures according to the invention (including one or more of the EP 151 series of preparations) were experimentally determined and the K and a values of the Mark-Houwink equation were determined by plotting (e.g. FIG. 7) as described below. The experimentally determined data demonstrate that the unique advantages of preferred oligomeric mixtures according to the invention have not previously been utilized or known. For purposes of illustration, the method of preparation of EP 1511, 1512, 151/49, 151/51, 151/52 according to the invention is described in detail immediately below.

a. CMC Hydrolysate EP1511 was prepared as described in Example 2c(i) hereinabove.

b. CMC Hydrolysate EP1512

20 kg of carboxymethylcellulose (CMC 7LFD-type, a cellulose gum, also designated by the tradename Blanose and available from Hercules Chemical Company, 92507, Rueil-Malmaison Ceder, France, 7LFD designating a low viscosity, food grade sodium carboxymethylcellulose having 7 out of 10 glucose units substituted with carboxymethyl group) was mixed in 250l of water and the pH of the solution was adjusted to 5.8 with 15% phosphoric acid and the temperature raised to 40° C. 0.177l of the above-described Trichoderma (Econase) enzyme preparation, having a total endo-1, 4 beta-glucanase activity of 1,780,000 nkat, was added to the CMC solution. After one hour another 20 kg of CMC was added to the solution. After hydrolysis for 23 hours the enzyme was inactivated by heating (90° C., 15 min.). Finally, the hydrolysis solution was concentrated by spray-drying.

c. CMC Hydrolysate EP 151/49

6 kg of sodium carboxymethylcellulose (CMC Finnfix 5, available from Metsä-Serla, Chemical Division, SF-44100 Äänekoski, Finland, representing food grade purity and having a degree of substitution between 0.6–0.8) was mixed with 240l of water. The pH of the solution was adjusted between 5.5 and 5.9 with 15% of phosphoric acid and the temperature was maintained at 40° C. 65ml of the above-described Trichoderma (Econase) enzyme preparation, the endo-$\beta$-1,4-glucanase activity of which totalled 539,000 nkat, was added to the CMC solution. After an hour another 6 kg of CMC was added. After hydrolysis for 23 hours, the enzyme was inactivated by heating the solution (90° C., 15 min.). The hydrolysate was then concentrated by spray-drying.

d. CMC Hydrolysate EP151/51

6 kg of sodium carboxymethylcellulose (CMC Finnfix 5) was mixed with 240l of water. Temperature and pH were as described with reference to preparation of EP151–49 (40° C., pH 5.5–5.9). 130 ml of the Trichoderma (Econase) enzyme preparation, the endo-$\beta$-1,4-glucanase activity of which totalled 1,079,000, was added to the CMC solution. After two hours another 6 kg of CMC was added. After hydrolysis for 47 hours the enzyme was inactivated by heating the solution (90° C., 15 min.). The hydrolysate was then concentrated by evaporating and spray-drying.

e. CMC Hydrolysate EP151/52

This hydrolysate was produced as described with reference to EP151-51, except that 195ml of the enzyme preparation containing an endo-$\beta$-1,4-glucanase activity of 1,618,000 nkat was used, and the hydrolysis time was 24 hours.

Chain Conformation Based on Prior Literature

The viscosities, the intrinsic viscosities, the viscosity average molecular weights ($M_v$) and the average degrees of polymerization of these various hydrolysate products are set forth in the following Table 2. As noted above, the average $M_v$ values set forth in Table 2 are calculated values. In general, suitable CMC oligomeric mixtures typically have an intrinsic viscosity of between about 50 ml/g and 3 ml/g in 0.2M sodium chloride and a viscosity value between about 5 and about 100 mPas (in 20% by weight solution at 25° C., shear rate $584_s{}^{-1}$. The viscosities were determined using a rotational viscometer (Haake Viscotester VT 500 with sensor system NV, Karlsruhe, Federal Republic of Germany). The intrinsic viscosities were measured according to the conventional method (described in Flory, *Principles of Polymer Chemistry*, Cornell Univ. Press, VII-4a, Ithaca, N.Y. (1953), the contents of which are incorporated by reference) at 25° C. by using a calibrated Cannon Fenske capillary viscometer (size 50, Cannon Instrument, State College, Pa., USA). The values of K and a for CMC, which were used in this study, were: K=0.043 in 0.2M NaCl and a=0.74 in 0.2M NaCl as described in the literature reference Brown and Henley, *Studies on Cellulose Derivatives Part IV. The Configuration of the Polyelectrolyte Sodium Chloride Solutions,* Macromol. Chem., Vol. 79, 00. 68–88 (1964) and as plotted in dotted line in FIG. 7.

TABLE 2

| CMC Hydrolysate | Viscosity[1] (mPas) | Intrinsic Viscosity[2] (ml/g) | Average $M_v$ | Average DP |
|---|---|---|---|---|
| 1511 | 32 | 31.4 | 7400 | 39 |
| 1512 | 20 | 22.9 | 4800 | 25 |
| 151/49 | 23 | 18.4 | 3600 | 19 |
| 151/51 | 18 | 14.0 | 2500 | 13 |
| 151/52 | 18 | 14.3 | 2600 | 13 |

1) 20% (w/w) solution, 25° C., shear rate = 584 s$^{-1}$
2) measured in 0.2M NaCl, 25° C.

Experimental Determination of Chain Conformation and Polydispersity

It is noted that a variety of methods for determining average molecular weight exist, and therefore the values of average molecular weights determined, as well as the average DP values calculated from them, depend upon the experimental method and the basis of calculation. For example, the number average molecular weight can be determined by end group analysis, osmotic pressure, vapor pressure lowering, boiling point elevation, freezing point depression and size exclusion chromatography. The weight average molecular weight can be determined by light scattering experiment, the viscosity average molecular weight from the size exclusion chromatograph. All these methods can be used for determining the average molecular weight which ultimately leads to the average DP values, although different results will be obtained depending on method and calculation used.

The $M_v$ values reported in Table 2 as determined on the basis of the literature value a=0.74 for CMC at 0.2N NaCl is higher than the true average molecular weights of the CMC hydrolysates listed. Experimental determination of weight average molecular weight ($M_w$) by multi angle light scattering measurement as described below shows that this conventional estimation method based on conventional literature values for k and a is not applicable to low molecular weight or relatively short chain polysaccharide derivative oligomers, i.e. rod-like, which are utilized in the most preferred embodiments of the invention.

Furthermore, the most preferred oligomeric mixtures according to the invention have a relatively narrow range of molecular weights, i.e. are relatively monodispersed, having a polydispersity index ($M_w/M_n$, weight average molecular weight divided by number average molecular weight) of less than about 2.0 and typically less than about 1.8. The weight average molecular weights and number average molecular weights of a variety of CMC hydrolysate samples of different degree of hydrolysis were measured and the polydispersity index of all such hydrolysates was calculated as ranging between about 1.1 and about 1.9. Therefore, the oligomers in a most preferred mixture of oligomers according to the invention extend over a relatively narrow range of $M_w$ and, even as to mixtures having an average molecular weight at or near the upper limit of $M_w$ where the oligomers may begin to assume a random coil configuration, are comprised of a significant portion, preferably a majority, of oligomers having a rod-like configuration.

The following materials were used in the experiments for this study to determine intrinsic viscosity at NaCl concentrations between 0.005 and 0.5N and weight average molecular weights, $M_w$.

I. Sodium Carboxymethyl Cellulose

| Raw or Starting Materials: | |
|---|---|
| Samples | Manufacturer |
| Blanose 7HFD | Hercules Chemical Company, France |
| Blanose 7MFD | Hercules Chemical Company, France |
| Blanose 7LFD | Hercules Chemical Company, France |
| Finnfix 5E | Metsa-Serla, Finland |
| Finnfix 2 (Lot No 59135) | Metsa-Serla, Finland |
| Finnfix 2 (Batch 59379-1) | Metsa-Serla, Finland |

| Hydrolysates: | |
|---|---|
| Samples | Descriptions |
| 151/70 1 h | hydrolysate of Blanose 7LFD |
| 151/70 2 hrs | hydrolysate of Blanose 7LFD |
| 1511 | hydrolysate of Blanose 7MFD |
| 1512 | hydrolysate of Blanose 7LFD |
| 151/63 1 h | hydrolysate of Blanose 7LFD |
| 151/63 4 hrs | hydrolysate of Blanose 7LFD |
| 151/63 24 hrs | hyrdolysate of Blanose 7LFD |
| 151/47 | hydrolysate of Finnfix 5E |
| 151/51 | hydrolysate of Finnfix 5E |
| 151/46 | hydrolysate of Finnfix 5E |
| 1512 Fr.A | fraction of hydrolysate 1512 |

II. Chemical Reagent Sodium Chloride (Analytical grade, Mallinckrodt, Paris, Ky.).

In the experimental determination of $M_w$ values, CMC solutions were prepared in 0.2N NaCl solution at pH of 7. The solutions were passed through an HPLC column, and the light intensity was detected by multiangle laser light scattering using a Wyatt Technology, multiangle laser light scattering instrument, model DAWN-F. The flow rate was 0.2 ml/min. The concentrations of the solutions were detected by refractometer, and the sensitivity of the refractometer was 64. The weight average molecular weights $M_w$, were determined using appropriate computer software and reported in Table 4.

The chain conformation of the most preferred CMC hydrolysates was studied using the Mark-Houwink equation $[\eta] = KM^a$. Again in the formula the variable n is instrinsic viscosity, K is a constant indicating the interaction between polymer and solvent, a is the Mark- Houwink exponent and M is the weight average molecular weight of the polymer. The Mark-Houwink exponent, a, was determined for each hydrolysate for purposes of classifying the oligomer configurations.

The instrinsic viscosities of the hydrolysates were measured from the concentration dependency of reduced viscosity. The reduced viscosity, specific viscosity divided by concentration of a hydrolysate solution, was determined using a Cannon capillary viscometer. The specific viscosity ($\eta_{sp}$) was calculated using the following formula $$\eta_{sp} = \frac{t}{t_o} - 1$$

wherein t is the flow time of the solution passing through the capillary viscometer and $t_o$ is the flow time of the solvent. The relationship between the reduced viscosity ($72_r$) and the concentration (c) is expressed as the following where [$\eta$] is the intrinsic viscosity:

$$\frac{\eta_{sp}}{c} = [\eta] + k^1[\eta]c$$

Therefore, the intrinsic viscosity was calculated by plotting the measured reduced viscosity versus various concentrations of hydrolysate solutions and the intercept of the plot at concentration of zero was the intrinsic viscosity of the hydrolysates tested.

Figure 7:
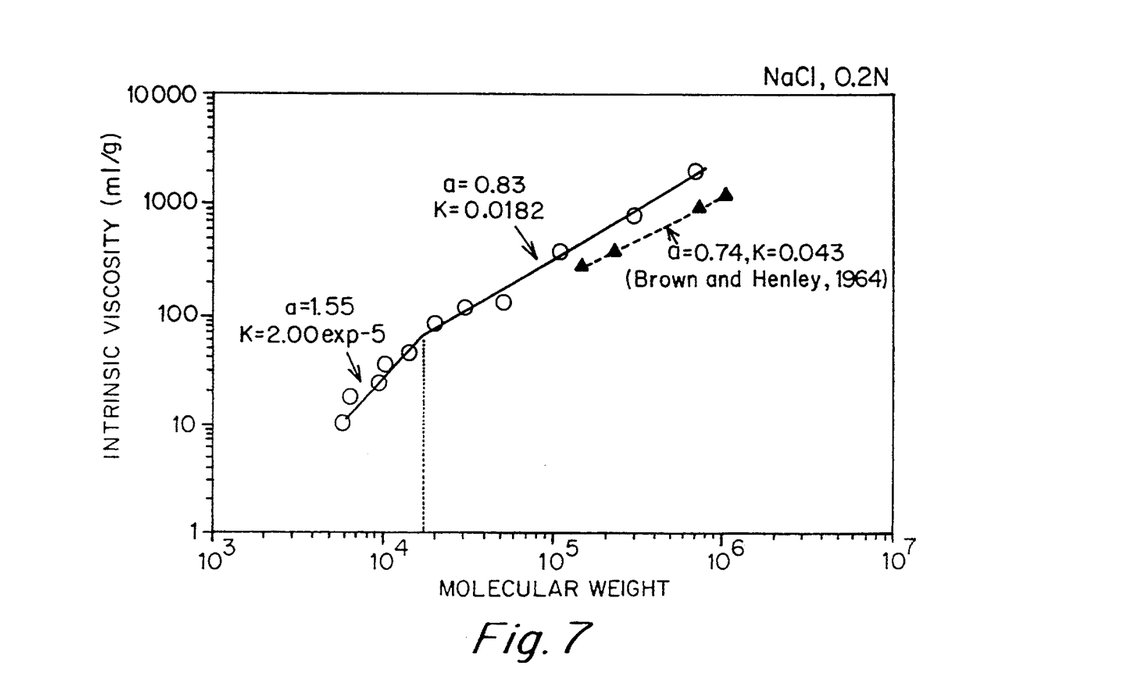
FIG. 7 is a log plot of intrinsic viscosity versus molecular weight as experimentally determined in solid line form for various CMC starting materials (a=0.83, K=0.0182) and hydrolysates (a=1.55, K=2.0 exp −5) in 0.2N solution of NaCl, also showing a dotted line plot for CMC assuming the K and a value for CMC as reported in the literature.

The Mark-Houwink exponent, a, and the constant, K, of the Mark-Houwink equation, [$\eta$]=KM$^a$, were determined for various CMCs such as listed in Table 4 (in solutions of varying concentration of NaCl) by plotting the log [$\eta$] versus the log of weight average molecular weight, $M_w$ (e.g. FIG. 7). $M_w$ was experimentally determined by multi angle light scattering instrument measuring as described above. The slope of the plot log [$\eta$] versus log [$M_w$] provides the exponent value a and the intercept of the plots at a theoretical log [$M_w$] of zero provides the value K. The a and K values thus determined are set forth in Table 3.

Chain Conformation

Figure 11:
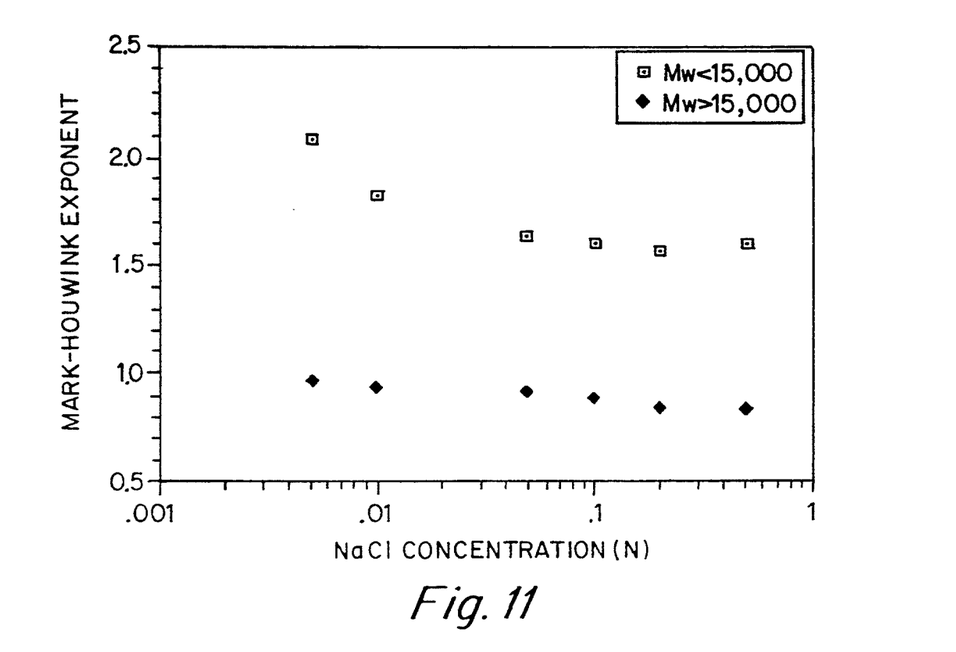
FIG. 11 is a plot of the Mark-Houwink exponent versus the NaCl concentration of CMC raw materials ( ) and CMC hydrolysates (□).

The dependency of the Mark-Houwink exponent on differences in salt concentration showed a difference between CMC raw materials and hydrolysates (Table 3 and FIGS. 7 and 11). The Mark-Houwink exponents for CMC raw or starting materials (having $M_w$ greater than about 15,000) are 0.97, 0.94, 0.91, 0.88, 0.83 and 0.83 at NaCl concentrations of 0.005, 0.010, 0.050, 0.100, 0.200 and 0.500N, respectively. In contrast, the Mark-Houwink exponents for CMC hydrolysates (having $M_w$ less than about 15,000) are 2.07, 1.82, 1.63, 1.59, 1.55 and 1.58 at NaCl concentrations of 0.005, 0.010, 0.050, 0.100, 0.200 and 0.500N, respectively. These values are approximately twice (2.13, 1.94, 1.79, 1.81, 1.87, 1.90 times) higher than those of CMC raw materials. The Mark-Houwink exponents of CMC raw materials decreased 14% over the NaCl concentration of 0.005N to 0.50N, while those of hydrolysates decreased 24% over the same range. Therefore, the decrease in the hydrolysates is 1.7 times higher than the CMC raw materials. Mark-Houwink exponents become a constant when the NaCl concentration is higher than 0.2N, probably having reached the unperturbed condition.

The Mark-Houwink exponents of 0.83-0.97 for CMC raw material ($M_w$>15,000 Daltons) indicate a free draining random coil conformation (left hand column of FIG. 6). In the random coil conformation, polymer coils are confined by the intra-chain interactions, therefore less change is seen in the Mark-Houwink exponent within the same range of ionic strength. However, when the weight average molecular weight is less than 15,000 Daltons, the CMC chain is not sufficiently long to form a winding coil, the polymer chain is no longer subjected to the constraint of intra-chain interactions, and a chain of free strip or rod-like configuration may form (right hand column of FIG. 6). When the ionic strength is low, the electrostatic repulsion force becomes dominant due to the negative charge of the carboxymethyl groups, and the polymer assumes its most stiff rod-like conformation with the highest value of the Mark-Houwink exponents (Table 3 and FIG. 6). When the ionic strength increases, the negative charge of carboxymethyl groups is shielded, the repulsion forces between the neighboring groups are reduced, and the polymer chains relax, yielding a lower Mark-Houwink exponent (Table 3 and FIG. 6).

The experimentally determined data, as described herein, and with reference to FIGS. 6-11, thus shows that the molecular weight and chain conformational characteristics of the most preferred polysaccharide derivative oligomeric mixtures of the invention, i.e. mixtures comprising a significant or substantial portion of oligomers of rod-like conformation, are distinctly different from polysaccharide polymer compositions previously known or employed in any application. Current understanding of the unique nature and properties of the relatively low molecular weight or short chain oligomers of the most preferred oligomeric mixtures utilized in the invention is lacking. As shown by the experimentally determined Mark-Houwink a values listed in Table 3 for weight average molecular weights, $M_w$, of CMC at less than about 15,000 daltons (a=1.58 to 2.07), the literature value of a=0.74 for CMC is erroneous with respect to CMC having a $M_w$ of less than about 15,000 daltons. This experimentally determined data quantitatively indicates that relatively short chain CMC assumes a rod-like configuration (right hand column of FIG. 6) as opposed to a free draining random coil conformation (left hand column of FIG. 6).

TABLE 3

Mark-Houwink Equations for CMC (25° C.)

| NaCl Concentration (N) | Weight Average Molecular Weight | |
|---|---|---|
| | >15,000 | <15,000 |
| 0.005 | [$\eta$] = 0.0069$M_w^{0.97}$ | [$\eta$] = 0.02 × 10$^{-5}M_w^{2.07}$ |
| 0.010 | [$\eta$] = 0.0084$M_w^{0.94}$ | [$\eta$] = 0.17 × 10$^{-5}M_w^{1.82}$ |
| 0.050 | [$\eta$] = 0.0090$M_w^{0.91}$ | [$\eta$] = 0.83 × 10$^{-5}M_w^{1.63}$ |
| 0.100 | [$\eta$] = 0.0116$M_w^{0.88}$ | [$\eta$] = 1.18 × 10$^{-5}M_w^{1.59}$ |
| 0.200 | [$\eta$] = 0.0182$M_w^{0.83}$ | [$\eta$] = 2.00 × 10$^{-5}M_w^{1.55}$ |
| 0.500 | [$\eta$] = 0.0179$M_w^{0.83}$ | [$\eta$] = 1.21 × 10$^{-5}M_w^{1.58}$ |

Chain Stiffness Parameter

Figure 8:
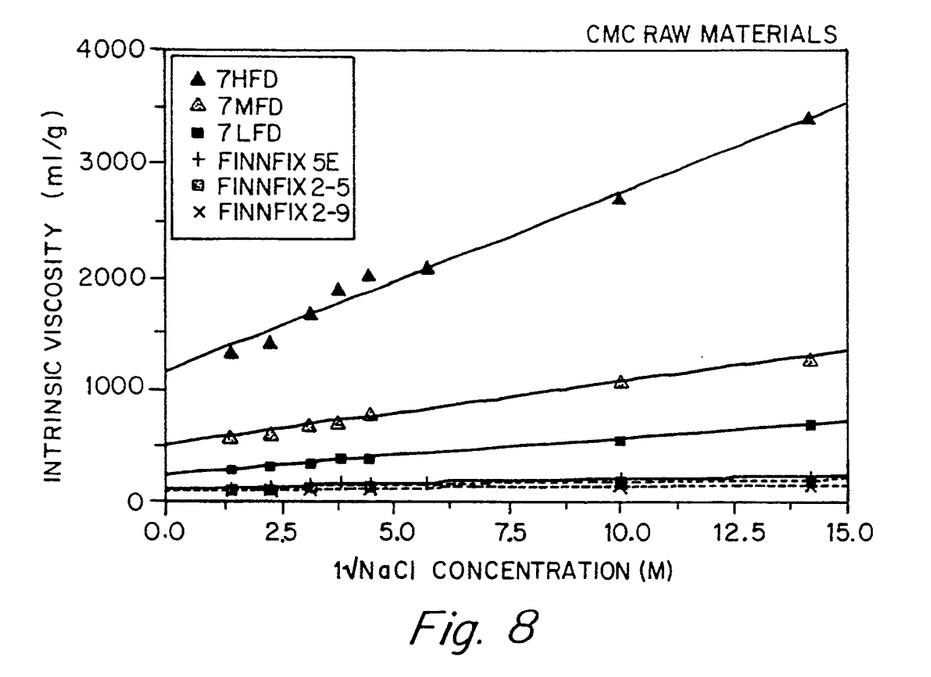
FIG. 8 is a plot of the intrinsic viscosity versus the square root of NaCl concentration of the CMC raw materials.
Figure 9:
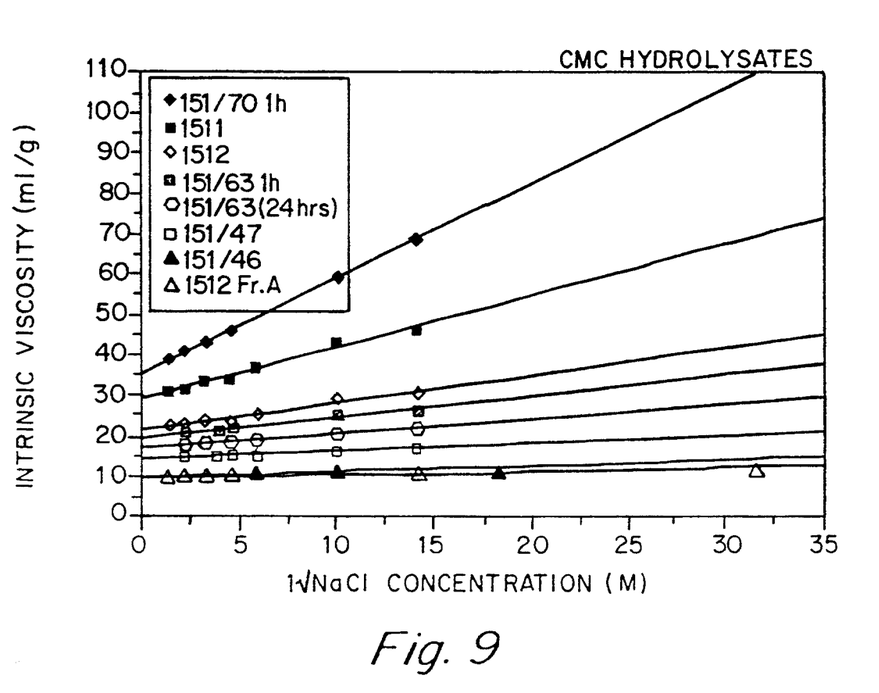
FIG. 9 is a plot of the intrinsic viscosity of the CMC hydrolysates versus the square root of the NaCl concentration.
Figure 10:
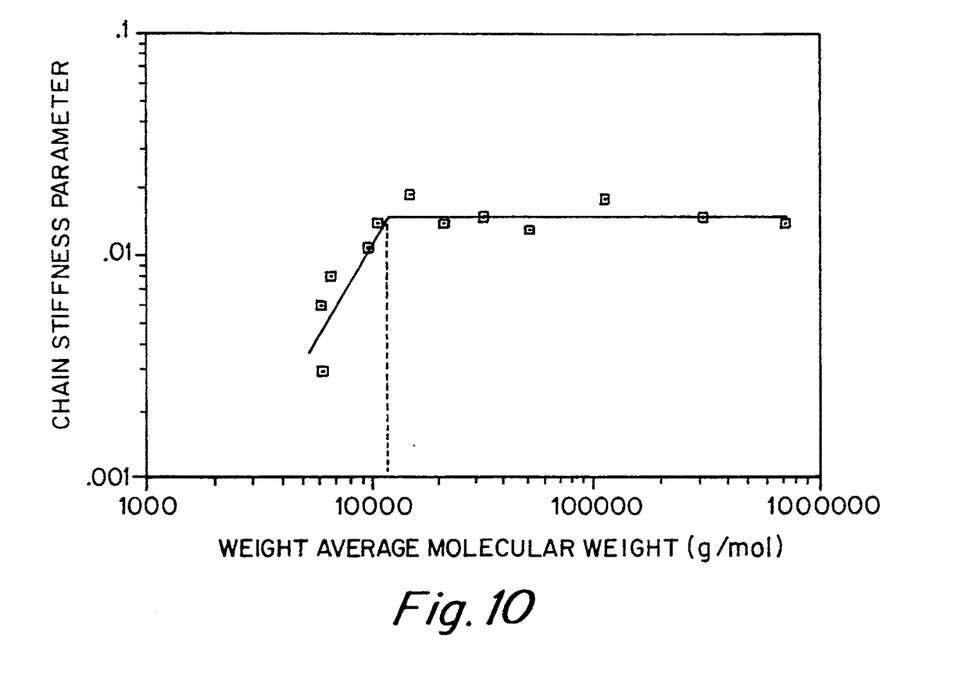
FIG. 10 is a log plot of the chain stiffness parameter versus the weight average molecular weight of CMC showing a transition occurring at a lower molecular weight.

The chain stiffness parameters are 0.014, 0.015, 0.018, 0.013, 0.015, 0.014, 0.019, 0.014, 0.011, 0.010, 0.008, 0.005, 0.006 and 0.003 for Blanose 7HFD, Blanose 7MFD, Blanose 7LFD, Finnfix 5E, Finnfix 2 (Lot#59135), Finnfix 2 (Batch 59379-1), 151/70 1h, 1511, 1512, 151/63 1h, 151/63 24 hrs, 151/47, 151/46 and 1512 Fr.A, respectively (Table 4). These chain stiffness parameters were calculated from the slopes of the plot between the intrinsic viscosity and the square root of NaCl concentration (FIG. 8 and FIG. 9). The relationship between the chain stiffness parameter and the weight average molecular weight shows a sudden decrease in the chain stiffness parameter when the weight average molecular weight becomes less than 10,000 Daltons (FIG. 10). This confirms that the conformational transition occurs, and low molecular weight CMC or CMC hydrolysate becomes significantly more stiff compared with higher molecular weight CMC. As shown repeatedly, ordinary CMC follows Gaussian chain distribution and behaves as a free draining random coil with Mark-Houwink exponents varying from 0.83–0.97. Upon hydrolysis, the low molecular weight CMC chain is no longer able to turn and the back bone forms a free strip, thereby relieving the intra-chain interactions (FIG. 6). Consequently, the conformation of the short chain corresponds to a rod-like shape with Mark-Houwink exponents varying from 1.2 to 2.0 and also results in the lower value of chain stiffness parameters. Experimental results (Table 4) show some deviation in the values of the chain stiffness parameter for higher molecular weight CMC. This may be due to the differences in the molecular weight distributions.

TABLE 4

The Chain Stiffness Parameter of CMC and CMC Hydrolysates

| CMC | $M_w$ | Chain Stiffness Parameter (B) |
|---|---|---|
| Raw Materials | | |
| 7HFD | 687,500 | 0.014 |
| 7MFD | 292,700 | 0.015 |
| 7LFD | 108,600 | 0.018 |
| Finnfix 5E | 50,200 | 0.013 |
| Finnfix 2 Lot#59135 | 30,700 | 0.015 |
| Finnfix 2 Batch 59379-1 | 20,200 | 0.014 |
| Hydrolysates | | |
| 151/70 1 h | 14,400 | 0.019 |
| 1511 | 10,400 | 0.014 |
| 1512 | 9,400 | 0.011 |
| 151/63-1 hr. | — | 0.010 |
| 151/63-24 hrs | 6,500 | 0.008 |
| 151/47 | — | 0.005 |
| 151/46 | 5,800 | 0.006 |
| 1512 Fr.A | 6,000 | 0.003 |

Example 4: Preparation of a Starch Precursor Hydrolyzate

Starch derivative hydrolyzates may be prepared from starch derivatives as defined above by an enzymatic hydrolysis utilizing an amylolytic preparation having α-amylase as the main active hydrolytic agent such that only insignificant amounts of mono- and disaccharides are produced. The hydrolysis procedure is generally carried out by dissolving the starch derivative in water, adjusting the pH and the temperature to the value suitable for the enzyme activity, adding the enzyme to the solution and allowing the enzyme to react for a suitable time. After the enzyme reaction, the enzyme is inactivated by heating the solution up to about 100° C. and the hydrolyzate product is concentrated and dried. The average degree of polymerization (DP) of the products formed by such a hydrolysis is less than 500 as determined by the reducing end group measurement, according to Somogyi, M. J. Biol. Chem. 195, 19–33, (1952). The specific conditions suitable for and the specific time sufficient to secure the desirable hydrolysis may be readily determined for each selected starch derivative and each selected enzyme preparation.

Similarly, where degradation is carried out using chemical or physical means, the average DP of the oligomers is less than 500.

60 g of carboxymethyl starch (CM starch) derived from potato starch (Primojel; Avebe, 9607 PT Foxhol, The Netherlands) was mixed in 1200 ml of water. The temperature of the mixture was raised to 80° C. and the suspension was mixed continuously. About 1.5 ml of amylase (Ban 120L, Novo, Industri A/S, Novo Alle, 2880 Bagsvaerd, Denmark) diluted 1/50 by volume was added to the suspension mixture. After hydrolysis of about 30 minutes the enzyme was inactivated by heating (100° C., 10 min.). The hydrolyzate was then freeze-dried.

The hydrolyzate had an average DP of about 350 as estimated from end group analysis (reducing sugar measurement) and contained negligible amounts of glucose, maltose and oligosaccharides, as the value of reducing sugars was 0.28%. The viscosity of a 5% by weight suspension of the hydrolyzate, measured using Haake-Rotovisco RV 12 viscometer with sensor systems NV; (Karlsruhe, Federal Republic of Germany) at 25° C. was 57 mPa.s using the shear rate of 692 1/s. The viscosity of the unhydrolysed raw CM starch material was 106 mPa.s <25° C., 692 1/s).

Example 5: Treatment of Paper with Polymers derived from Carboxymethyl cellulose (CMC)

Ten percent by weight of carboxymethyl cellulose hydrolyzate (intrinsic viscosity=31.4 ml per gram; average DP of about 50) dispersion was prepared with deionized water by stirring overnight. The process was carried out by dipping Whatman No. 1 filter paper in the hydrolyzate dispersion in water for 5 minutes. After dipping, the papers were dried in an oven overnight. Three paper samples (hydrolyzate treated, water treated, and untreated papers) were tested for tensile strength, strain limit, modulus, and water and oil spreading. For the tensile test, paper was cut to 50×2 mm and loaded in the grip of an Instron Universal Testing Machine (Model 1122, Canton Mass. 02021).

Results

After dipping into hydrolyzate solution, the treated paper was dried and tested. (Tables 5 and 6).

TABLE 5

The Change in Properties* of Paper Treated with Carboxymethyl Cellulose Hydrolyzate (CMC)

| Sample Paper | Maximum Tensile Strength (atm) | Tangential Modulus (atm/%) | Strain Limit (%) |
|---|---|---|---|
| CMC Hydrolyzate #1 | 286 | 168 | 3.6 |
| CMC Hydrolyzate #2 | 385 | 184 | 4.2 |
| CMC Hydrolyzate #3 | 297 | 211 | 3.0 |
| Water | 120 | 73 | 3.9 |
| Untreated | 160 | 90 | 2.7 |

*Values are the average of 10 tests for each sample.

Figure 1:
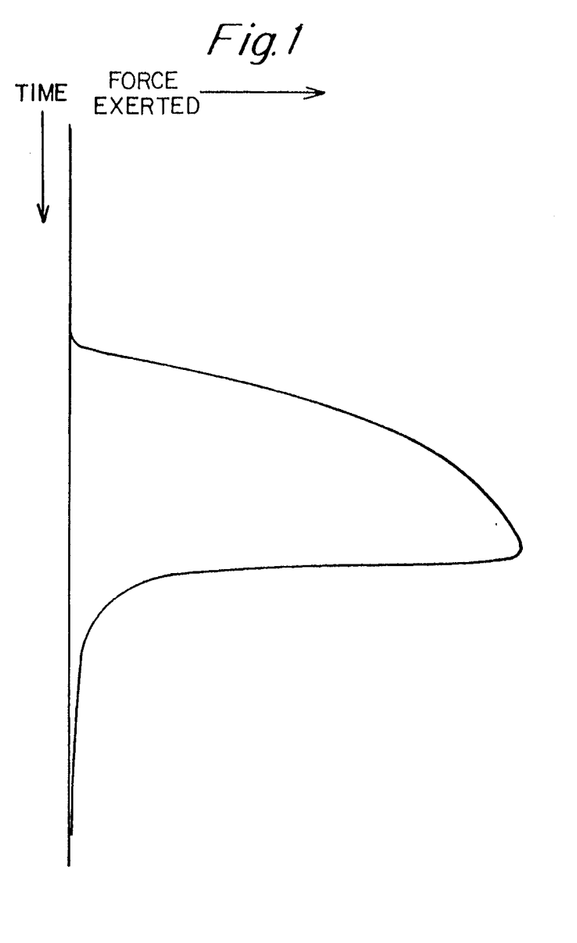
FIG. 1 is a force-distance curve of Whatman No. 1 filter paper treated with carboxylmethyl cellulose hydrolyzate.
Figure 2:
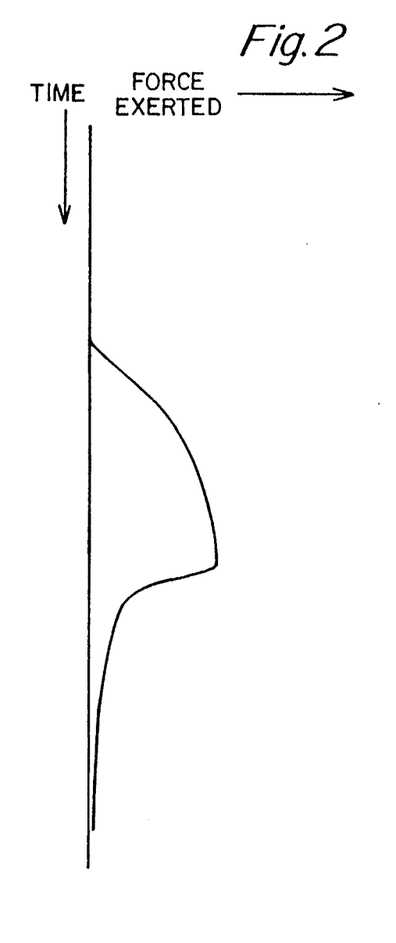
FIG. 2 is a force-distance curve of Whatman No. 1 filter paper dipped in distilled water.
Figure 3:
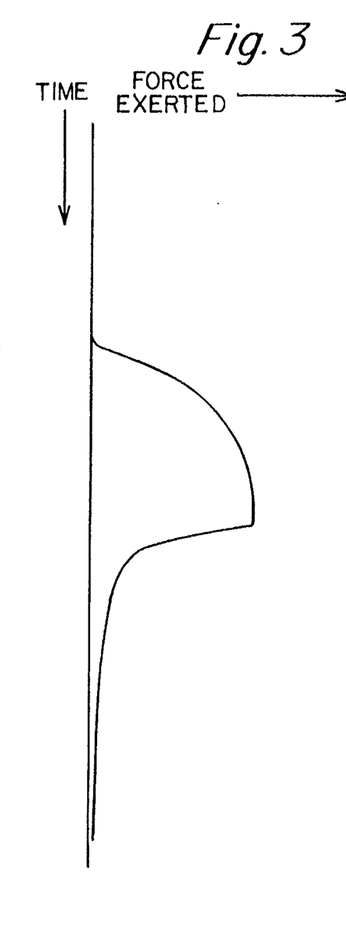
FIG. 3 is a force-distance curve of untreated Whatman No. 1 filter paper.

Force-elongation tests were performed with a cross-head speed of 5 mm min$^{-1}$, a chart speed of 500 mm min$^{-1}$, and a maximum load of 2000 $g_f$. FIGS. 1, 2, 3 for hydrolyzate-treated, water-treated, and untreated papers, respectively. The resultant values of the maximum tensile strength before rupturing of treated paper showed a 2 to 3 fold increase over untreated or water treated papers when the paper was treated with the hydrolyzate. Also, the strain limit and modulus increased by dipping paper in hydrolyzate (Table 5). Dipping paper in water alone decreased the mechanical strength and increased the strain limit (Table 5).

Water and oil spreading on the papers were also tested (Table 6). Paper dipped in the water did not show any difference in water spreading compared to untreated paper. However, it showed more spreading of oil compared to untreated paper. Hydrolyzate-dipped paper showed much less water spreading than untreated paper.

TABLE 6

Water and oil spreading* on treated and untreated papers

| Sample | Water spreading[1] (diameter, mm) | Oil spreading[2] (diameter, mm) |
|---|---|---|
| Carboxymethyl cellulose hydrolyzate-treated | 13 | 26 |
| Water-treated | 21 | 25 |
| Untreated | 20 | 23 |

*Average of Triplicate (± s.e.)
[1]Measured diameter 5 minutes after spotting 20 μl of water.
[2]Measured diameter 30 minutes after spotting 20 μl of oil.

Example 6: Treatment of Paper with Polymers derived from Carboxymethyl Starch (CMS)

Five percent carboxymethyl starch (CMS) and carboxymethyl starch hydrolyzate (CMSH) of Example 4 dispersions were prepared with deionized water. Two sets of dispersions were made; one was mixed (10 minutes) at room temperature and the other at 90° C. (to achieve gelatinization). The coating process was carried out by dipping Whatman No. 1 filter paper in each polymer dispersion for 5 minutes. After dipping, the papers were dried in an oven overnight. The paper samples were tested for tensile strength, strain limit and modulus. For the tensile test, paper was cut to 50×2 mm and loaded in the grip of an Instron Universal Testing Machine (Model 1122, Canton, Mass. 02021).

In both sets of samples prepared at room temperature and at 90° C., the paper treated with carboxymethyl starch hydrolyzate had higher tensile strength and strain limit than the paper treated with carboxymethyl starch of higher molecular weight. (Table 7). This shows, that the mechanical properties of the paper can be improved more using carboxymethyl starch or lower molecular weight. Also the modulus was higher when the paper was treated with carboxymethyl starch hydrolyzates, suggesting an increase in the stiffness of the paper (Table 7).

TABLE 7

The Change in Properties* of Paper Treated with Carboxymethyl Starch Hydrolyzate

| Sample Paper | Maximum Tensile Strength (atm) | Strain Limit (%) | Tangential Modulus (atm/%) |
|---|---|---|---|
| CM Starch (room temp.) | 79 | 3.2 | 48 |
| CM Starch (90° C.) | 80 | 4.9 | 43 |
| CM Starch Hydrolyzate (CMSH) (room temp.) | 209 | 5.2 | 130 |
| CM Starch Hydrolyzate CMSH (90° C.) | 234 | 6.9 | 117 |

Example 7: Hydrolyzed Polysaccharide Derivatives as Dewatering Aids

Polysaccharide derivatives or their hydrolyzates were prepared (for CMC hydrolysates according to Example 2(c)(i); for CM starch hydrolysates according to Example 4) and dissolved in water. After stirring for 10 minutes, the solution was added to furnish. The final mixture contained furnish (0.106% w/v solid) and 0.0053% (w/v) polysaccharide derivatives or their hydrolyzates. The mixture was mixed for 10 minutes and poured on basement paper which serves as a screen. The amount of water drained was recorded for the determination of dewatering rate and final water content was measured. The furnish was dried in the oven and used in the tensile strength test.

Figure 4:
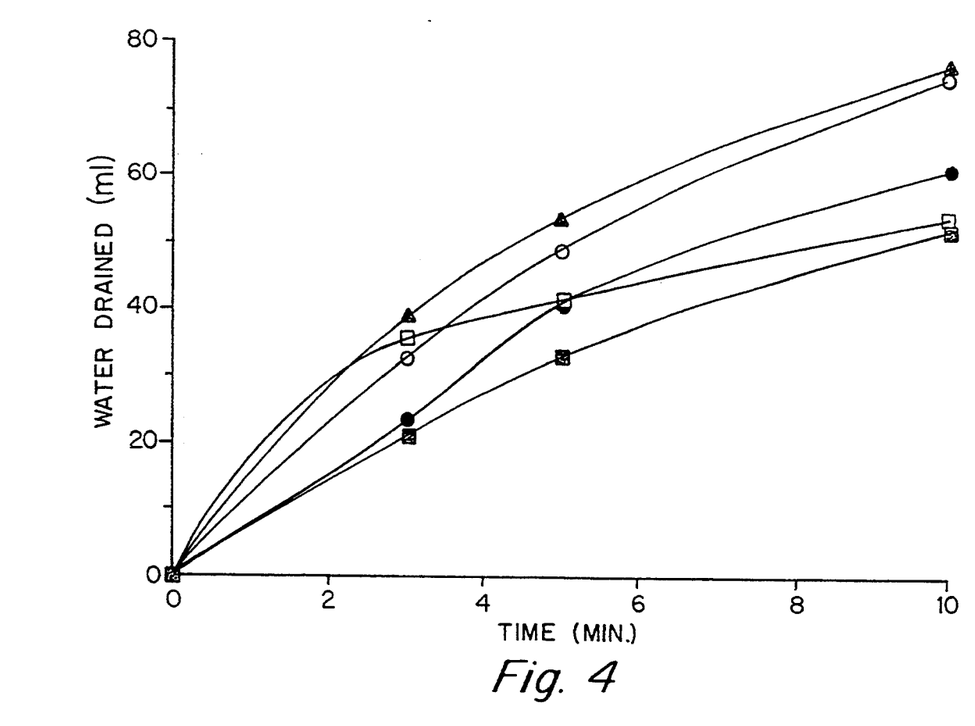
FIG. 4 shows results of drainage tests on furnish treated with carboxymethyl cellulose (CMC) hydrolyzate (●), carboxymethyl cellulose (o), carboxymethyl starch (CM starch) hydrolyzate (■), carboxymethyl starch (CM starch) (△), and untreated furnish (□).

Drainage tests for furnish treated with charged polysaccharides and with their hydrolyzates showed initial drainage rates higher than that of furnish alone. (FIG. 4).

The amount of drained water (i.e. an index of dewatering) and the water content of the furnish (i.e. an index of draining) treated with charged polysaccharide derivatives and their hydrolyzates are shown in Table 8.

TABLE 8

| Furnish Treatment | Amount of Water Drained (ml) | Weight of Retained Water (g) (Final Water Content) |
|---|---|---|
| CMC Hydrolyzate | 95 | 5.3 |
| CMC | 92 | 4.5 |
| CM Starch Hydrolyzate | 94 | 6.2 |
| CM Starch | 94 | 5.4 |
| Control (Furnish) | 93 | 5.0 |

Tensile strength tests showed that the furnish treated with charged polysaccharide hydrolyzates gave higher tensile strength and tangential modulus than those tested with high molecular weight charged polysaccharides (Table 7).

TABLE 9

| Sample Furnish Treatment | Maximum Tensile Strength (atm) | Strain Limit (%) | Modulus (atm %) |
|---|---|---|---|
| CMC Hydrolyzate | 114.0 | 4.7 | 60 |
| CMC | 75.8 | 5.5 | 33 |
| CM Starch Hydrolyzate | 100.0 | 4.7 | 58 |
| CM Starch | 85.7 | 4.3 | 46 |
| Control (Furnish) | 88.4 | 4.7 | 51 |

Therefore, this experiment shows that polysaccharide derivatives and their hydrolyzate increase the rate of dewatering in the early stage of drainage. Particularly, the polysaccharide derivative hydrolyzates of the invention significantly improve the mechanical properties of the pulp product.

Example 8

Figure 5:
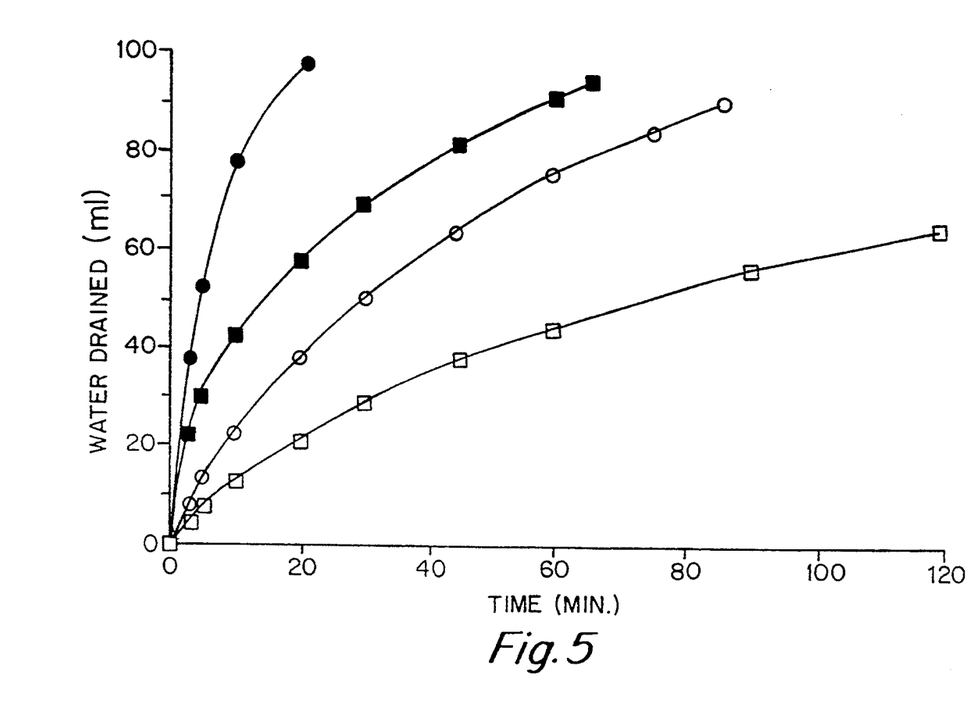
FIG. 5 shows results of drainage tests on furnish/calcium carbonate mixtures treated with carboxymethyl cellulose (CMC) hydrolyzate (●), carboxymethyl cellulose (o), carboxymethyl starch (CM starch) hydrolyzate (■), and carboxymethyl starch (CM starch) (□).

Polysaccharides or their hydrolyzates were prepared (for CMC hydrolysates according to Example 2(c)(i); for CM starch hydrolysates according to Example 4) and dissolved in a warm water (80° C., CM starch and its hydrolyzate) or room temperature water (CMC and its hydrolyzate). After stirring for 10 minutes, the solution was mixed with $Ca(CO_3)_2$ solution. After stirring for 10 minutes, the mixture was added to furnish. The mixture contained furnish with 0.106% (w/v) solid, 0.106% (w/v) $Ca(CO_3)_2$, and 0.00575% (w/v) polysaccharides or their hydrolyzates. The test for dewatering was repeated. The draining rates were faster in those mixtures containing hydrolyzate than those of high molecular weight polysaccharides (FIG. 5).

The amount of drained water, and the final water content of the samples treated with charged polysaccharides and their hydrolyzates are shown in Table 10. Furnish and $Ca(CO_3)_2$ treated with hydrolyzates showed a higher dewatering rate, retaining less water than furnish and $Ca(CO_3)_2$ treated with higher molecular weight polysaccharide derivatives.

TABLE 10

| Furnish Mixture Treatment | Amount of Water Drained (ml) | Weight of Retained Water (g) (Final Water Content) |
|---|---|---|
| CMC Hydrolyzate | 98 | 4.3 |
| CMC | 90 | 5.5 |
| CM Starch Hydrolyzate | 94 | 6.4 |
| CM Starch | 89 | 7.4 |

The furnish mixture thus produced were dried in an oven and the tensile strength was tested. The test results showed that the samples treated with charged polysaccharide hydrolyzates had a higher tensile strength and tangential modulus than those treated with high molecular weight charged polysaccharide for both CMC and CM starch (Table 11).

TABLE 11

| Sample Paper | Maximum Tensile Strength (atm) | Strain Limit (%) | Tangential Modulus (atm/%) |
|---|---|---|---|
| CMC Hydrolyzate | 81.2 | 4.5 | 43 |
| CMC | 61.4 | 4.4 | 35 |
| CM Starch Hydrolyzate | 101.7 | 5.0 | 61 |
| CMS | 85.7 | 5.6 | 49 |
| Control (Furnish) | 88.4 | 4.7 | 51 |

It will now be apparent to those skilled in the art that other embodiments, improvements, details and uses can be made consistent with the letter and spirit of the foregoing disclosure and within the scope of this patent, which is limited only by the following claims, construed in accordance with the patent law, including the doctrine of equivalents.

What is claimed is:

1. A paper product treated with a degradation product of a cellulose derivative comprising a mixture of oligomers of the cellulose derivative, a majority of said oligomers having a degree of polymerization of between about 5 and about 50.

2. A paper product as claimed in claim 1 wherein the degradation product consists essentially of the mixture of oligomers.

3. A paper product as claimed in claim 1 wherein the cellulose derivative has at least one substituent selected from the group consisting of carboxymethyl, methyl, hydroxypropyl, amino, methylethyl, hydroxyethyl, hydroxymethylethyl, hydroxypropylmethyl, hydroxypropylethyl, sulfate, carboxylic acid, carboxylic acid ester and pyruvate.

4. A paper product as claimed in claim 1 wherein the cellulose derivative is selected from the group consisting of carboxymethyl cellulose, ethylmethyl cellulose, hydroxypropylethyl cellulose, methyl cellulose, hydroxypropyl cellulose, hydroxypropylmethyl cellulose, hydroxymethylethyl cellulose and mixtures thereof.

5. A paper product as claimed in claim 4 wherein the cellulose derivative is carboxymethyl cellulose.

6. A paper product as claimed in claim 5 wherein the mixture of oligomers has an average molecular weight of less than about 15,000 daltons.

7. A paper product as claimed in claim 1 wherein the mixture of oligomers have a molecular weight distribution such that the mixture has a polydispersity index of less than about two and the degradation product contains less than about 25% by weight of monosaccharides, disaccharides or mixtures thereof.

8. A paper product as claimed of claim 7 wherein the degradation product contains less than about 10% by weight of monosaccharides, disaccharides or mixtures thereof.

9. A method of increasing the strength of paper comprising,
treating the paper with a degradation product of a cellulose derivative comprising a mixture of oligomers of the cellulose derivative, a majority of the oligomers having a degree of polymerization between about 5 and about 50.

10. A method as claimed in claim 9 further comprising treating the paper with additional agents selected from the group consisting of dyes, colorants, wet-strength agents, and defoamers.

11. A method as claimed in claim 9 wherein the treatment step involves coating the paper by dipping, spraying, rolling or admixing.

12. In a method of paper manufacture having the steps of:
(a) pulping the fibers;
(b) refining the paper stock;
(c) forming the paper sheet; and
(d) drying the paper sheet,
the improvement comprising: treating the paper with a degradation product of a cellulose derivative comprising a mixture of oligomers of the cellulose derivative, a majority of said oligomers having a degree of polymerization between about 5 and 50.

13. A method as claimed in claim 12 wherein in the treatment step the cellulose derivative has at least one substituent selected from the group consisting of carboxymethyl, methyl, amino, hydroxypropyl, methylethyl, hydroxypropylethyl, hydroxyethyl, hydroxypropymethyl, hydroxymethylethyl, hydroxypropylmethyl, sulfate, carboxylic acid, carboxylic acid ester and pyruvate.

14. A method as claimed in claim 12 wherein the treatment step is an impregnating step.

15. A method as claimed in claim 12 wherein the treatment step is a coating step.

16. A method as claimed in claim 15 wherein the coating step is dipping, spraying, rolling or admixing.

17. A method as claimed in claim 12 wherein the cellulose derivative is selected from the group consisting of carboxymethyl cellulose, ethylmethyl cellulose, hydroxypropylethyl cellulose, methyl cellulose, hydroxypropyl cellulose, hydroxypropylmethyl cellulose, hydroxymethylethyl cellulose and mixtures thereof.

18. A method as claimed in claim 17 wherein the cellulose derivative is carboxymethyl cellulose.

19. A method as claimed in claim 18 wherein the mixture of oligomers has an average molecular weight of less than about 15,000 daltons.

20. A method as claimed in claim 12 wherein the mixture of oligomers have molecular weight distribution such that the mixture has a polydispersity index of less than about two and the degradation product contains less than about 25% by weight of monosaccharides, disaccharides or mixtures thereof.

21. A method as claimed of claim 20 wherein the degradation product contains less than about 10% by weight of monosaccharides, disaccharides or mixtures thereof.

22. A method of increasing the dewatering properties of a paper product, comprising treating the paper product with a degradation product of a cellulose derivative comprising a mixture of oligomers of the cellulose derivative, a majority of said oligomers having a degree of polymerization between about 5 and about 50.

23. A method as claimed in claim 22 further comprising treating the paper with at least one additive selected from the group consisting of dyes, colorants, wet-strength agents and defoamers.

24. A method as claimed in claim 22 wherein in the treatment step, the cellulose derivative has at least one substituent selected from the group consisting of carboxymethyl, methyl, amino hydroxypropyl, methylethyl, hydroxyethyl, hydroxypropylethyl hydroxymethylethyl, hydroxypropylmethyl, sulfate, carboxylic acid, carboxylic acid ester and pyruvate.

25. A method as claimed in claim 22 wherein the treatment step comprises combining the mixture of oligomers with furnish.

26. A method as claimed in claim 22 wherein the paper product is selected from the group consisting of pulp, a finished paper, textile products and other cellulose based products.

27. A paper product treated with a degradation product of a cellulose derivative comprising a mixture of oligomers of the cellulose derivative the majority of which have a Mark-Houwink exponent of at least 1.2 at an NaCl concentration of about 0.005N to 0.5N.

28. A paper product as claimed in claim 27 wherein the celluose derivative has at least one substituent selected from the group consisting of carboxymethyl, methyl, hydroxypropyl, amino, methylethyl, hydroxyethyl, hydroxypropylethyl, hydroxymethylethyl, hydroxypropylmethyl, sulfate, carboxylic acid, carboxylic acid ester and pyruvate.

29. A paper product as claimed in claim 27 wherein the cellulose derivative is selected from a group consisting of carboxymethyl cellulose, methyl cellulose, hydroxypropyl cellulose hydroxypropylethyl cellulose, methyethyl cellulose, hydroxypropylmethyl cellulose, hydroxymethylethyl cellulose and mixtures thereof.

30. A paper product as claimed in claim 29 wherein the cellulose derivative is carboxymethyl cellulose.

31. A paper product as claimed in claim 30 wherein the mixture of oligomers has an average molecular weight of less than about 15,000 daltons.

32. A paper product as claimed in claim 27 wherein the mixture of oligomers have molecular weight distribution such that the mixture has a polydispersity index of less than about two and the degradation product contains less than about 25% by weight of monosaccharides, disaccharides or mixtures thereof.

33. A paper product as claimed of claim 32 wherein the degradation product contains less than about 10% by weight of monosaccharides, disaccharides or mixtures thereof.

34. A method of increasing the strength of paper comprising,
    treating the paper with a degradation product of a cellulose derivative comprising a mixture of oligomers of the cellulose derivative, a majority of said oligomers having a Mark-Houwink exponent of at least 1.2 at an NaCl concentration of about 0.005N to about 0.5N.

35. A method as claimed in claim 34 further comprising treating the paper with at least one additional agent selected from the group consisting of dyes, colorants, wet strength agents and defoamers.

36. A method as claimed in claim 34 wherein the treatment step involves coating the paper by dipping, spraying, rolling or admixing.

37. In a method of paper manufacture having the steps of:
    (a) pulping the fibers;
    (b) refining the paper stock;
    (c) forming the paper sheet;
    (d) drying the paper sheet,
    the improvement comprising treating the paper with a degradation product of a cellulose derivative comprising a mixture of oligomers of the cellulose derivative, a majority of the oligomers having a Mark-Houwink exponent of at least 1.2 at an NaCl concentration of about 0.005N to about 0.5N.

38. A method as claimed in claim 37 wherein in the treatment step the cellulose derivative has at least one substituent selected from the group consisting of carboxymethyl, methyl, amino, hydroxypropyl, methylethyl, hydroxyethyl, hydroxypropylethyl, hydroxymethylethyl, hydroxypropylmethyl, sulfate, carboxylic acid, carboxylic acid ester and pyruvate.

39. A method as claimed in claim 37 wherein the treatment step is an impregnating step.

40. A method as claimed in claim 37 wherein the treatment step is a coating step.

41. A method as claimed in claim 40 wherein the coating step is dipping, spraying, rolling or admixing.

42. A method as claimed in claim 37 wherein the mixture of oligomers have molecular weight distribution such that the mixture has a polydispersity index of less than about two and the degradation product contains less than about 25% by weight of monosaccharides, disaccharides or mixtures thereof.

43. A method as claimed in claim 42 wherein the degradation product contains less than about 10% by weight of monosaccharides, disaccharides or mixtures thereof.

44. A method as claimed in claim 37 wherein the cellulose derivative is carboxymethyl cellulose.

45. A paper product as claimed in claim 44 wherein the mixture of oligomers has an average molecular weight of less than about 15,000 daltons.

46. A method of increasing the dewatering properties of paper, comprising treating the paper with a degradation product of a cellulose derivative comprising a mixture of oligomers of the cellulose derivative, a majority of which have a Mark-Houwink exponent of at least 1.2 at an NaCl concentration of about 0.005N to about 0.5N.

47. A method as claimed in claim 46 further comprising treating the paper with at least one additive selected from the group consisting of dyes, colorants, wet-strength agents and defoamers.

48. A method as claimed in claim 46 wherein in the treatment step, the cellulose derivative has at least one substituent selected from the group consisting of carboxymethyl, methyl, amino, hydroxypropyl, methylethyl, hydroxyethyl, hydroxypropylethyl, hydroxymethylethyl, hydroxypropylmethyl, sulfate, carboxylic acid, carboxylic acid ester and pyruvate.

49. A method as claimed in claim 46 wherein the treatment step comprising combining the mixture of oligomers with furnish.

50. A method as claimed in claim 46 wherein the paper product is selected from the group consisting of pulp, a finished paper product, textile products and other cellulose based products.

51. A paper product treated with a degradation product of cellulose derivative comprising a mixture of oligomers of the cellulose derivative, the majority of which have a degree of polymerization in the range of about 5 to about 50 and a rod-like configuration.

52. A paper product as claimed in claim 51 wherein the cellulose has at least one substituent selected from the group consisting of carboxymethyl, methyl, hydroxypropyl, hydroxypropylethyl, amino, methylethyl, hydroxyethyl, hydroxymethylethyl, hydroxypropylmethyl, sulfate, carboxylic acid, carboxylic acid ester and pyruvate.

53. A paper product as claimed in claim 51 wherein the cellulose derivative is selected from the group consisting of carboxymethyl cellulose, methyl cellulose, hydroxypropyl cellulose, hydroxypropylmethyl cellulose, methylethyl cellulose, hydroxypropylethyl cellulose, hydroxymethylethyl cellulose and mixtures thereof.

54. A paper product as claimed in claim 51 wherein the cellulose derivative is carboxymethyl cellulose.

55. A method of increasing the strength of paper comprising,
treating the paper with a degradation product of a cellulose derivative comprising a mixture of oligomers, the majority of which have a degree of polymerization in the range of about 5 to about 50 and a rod-like configuration.

56. A method as claimed in claim 55 further comprising treating the paper with at least one additional agent selected from the groups consisting of dyes, colorants, wet strength agents and defoamers.

57. A method as claimed in claim 55 wherein the treatment step involves coating the paper by dipping, spraying, rolling or admixing.

58. In a method of paper manufacture having the steps of:
(a) pulping the fibers;
(b) refining the paper stock;
(c) forming the paper sheet; and
(d) drying the paper sheet,
the improvement comprising treating the paper with a degradation product of a cellulose derivative comprising a mixture of oligomers, the majority of which have a degree of polymerization in the range of about 5 and about 50 and a rod-like configuration.

59. A method as claimed in claim 58 wherein in the treatment step the cellulose derivative has at least one substituent selected from the group consisting of carboxymethyl, methyl, amino, hydroxypropyl, methylethyl, hydroxyethyl, hydroxymethylethyl, hydroxypropylmethyl, hydroxypropylethyl, sulfate, carboxylic acid, carboxylic acid ester and pyruvate.

60. A method as claimed in claim 58 wherein the treatment step is an impregnating step.

61. A method as claimed in claim 58 wherein the treatment step is a coating step.

62. A method as claimed in claim 61 wherein the coating is dipping, spraying, rolling or admixing.

63. A method of increasing the dewatering properties of paper, comprising treating the paper with a degradation product of a cellulose derivative comprising a mixture of oligomers, the majority of which have a degree of polymerization in the range of about 5 and about 50 and a rod-like configuration.

64. A method as claimed in claim 63 further comprising treating the paper with at least one additive selected from a group consisting of dyes, colorants, wet-strength agents and defoamers.

65. A method as claimed in claim 63 wherein in the treatment step the cellulose derivative has at least one substituent selected from the group consisting of carboxymethyl, methyl, amino, hydroxypropyl, methylethyl, hydroxyethyl, hydroxymethylethyl, hydroxypropylmethyl, hydroxypropylethyl, sulfate, carboxylic acid, carboxylic acid ester and pyruvate.

66. A method as claimed in claim 63 wherein the treatment step further comprises combining the mixture of oligomers with furnish.

67. A method as claimed in claim 63 wherein the paper product is selected from the group consisting of pulp, a finished paper product, textile products, and other cellulose based products.

* * * * *